US011311177B2

(12) United States Patent
Takatsuji et al.

(10) Patent No.: US 11,311,177 B2
(45) Date of Patent: Apr. 26, 2022

(54) ENDOSCOPE AND ENDOSCOPE SYSTEM

(71) Applicant: OLYMPUS CORPORATION, Tokyo (JP)

(72) Inventors: Kenji Takatsuji, Tokyo (JP); Chikayoshi Meguro, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 16/355,897

(22) Filed: Mar. 18, 2019

(65) Prior Publication Data

US 2019/0208988 A1 Jul. 11, 2019

Related U.S. Application Data

(63) Continuation of application No. PCT/JP2017/029758, filed on Aug. 21, 2017.

(30) Foreign Application Priority Data

Dec. 14, 2016 (JP) .............................. JP2016-242111

(51) Int. Cl.
*A61B 1/00* (2006.01)
*A61B 1/005* (2006.01)
(Continued)

(52) U.S. Cl.
CPC ........ *A61B 1/0052* (2013.01); *A61B 1/00006* (2013.01); *A61B 1/00039* (2013.01);
(Continued)

(58) Field of Classification Search
CPC . A61B 1/0052; A61B 1/0011; A61B 1/00112; A61B 1/00121; A61B 1/00128;
(Continued)

(56) References Cited

U.S. PATENT DOCUMENTS 4,617,915 A * 10/1986 Arakawa ............ A61B 1/00066
600/131
2006/0252993 A1* 11/2006 Freed ................ A61M 25/0147
600/146

(Continued)

FOREIGN PATENT DOCUMENTS

JP 2002-253563 A 9/2002
JP 2004-358011 A 12/2004
(Continued)

OTHER PUBLICATIONS

International Search Report dated Oct. 3, 2017 issued in PCT/JP2017/029758.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope includes: an endoscope operation portion; a first grasping portion configured to enable the endoscope operation portion to be grasped in a first grasping state; a second grasping portion configured to enable the endoscope operation portion to be grasped in a second grasping state; and attaching portion mounting portions to which an attaching portion of a treatment instrument operation portion is attached so as to enable an operation of the bending operation lever and an operation of a slider provided to the treatment instrument operation portion of the treatment instrument to be performed with fingers of a hand grasping the first grasping portion or the second grasping portion, the attaching portion mounting portions being formed respectively on the first grasping portion and the second grasping portion.

8 Claims, 5 Drawing Sheets

(51) Int. Cl.
  *A61B 1/018* (2006.01)
  *A61B 17/221* (2006.01)
  *A61B 17/00* (2006.01)

(52) U.S. Cl.
  CPC ...... *A61B 1/00066* (2013.01); *A61B 1/00133* (2013.01); *A61B 1/018* (2013.01); *A61B 17/221* (2013.01); *A61B 1/00087* (2013.01); *A61B 2017/00477* (2013.01)

(58) Field of Classification Search
  CPC ............ A61B 1/00131; A61B 1/00133; A61B 1/00137; A61B 1/0014; A61B 1/018; A61B 1/012; A61B 1/01; A61B 17/221; A61B 2017/00477
  USPC ................................ 600/131, 146, 104, 153
  See application file for complete search history.

(56) References Cited

U.S. PATENT DOCUMENTS

| | | | |
|---|---|---|---|
| 2014/0221739 A1* | 8/2014 | Yamada | A61B 17/00234 600/106 |
| 2017/0086651 A1 | 3/2017 | Sato et al. | |
| 2017/0143188 A1* | 5/2017 | Oskin | A61B 1/00128 |

FOREIGN PATENT DOCUMENTS

| | | | |
|---|---|---|---|
| JP | 2005-168882 A | 6/2005 | |
| JP | 2007-151595 A | 6/2007 | |
| WO | 2015/194486 A1 | 12/2015 | |

\* cited by examiner

ENDOSCOPE AND ENDOSCOPE SYSTEM

CROSS REFERENCE TO RELATED APPLICATION

This application is a continuation applicant of PCT/JP2017/029758 filed on Aug. 21, 2017 and claims benefit of Japanese Application No. 2016-242111 filed in Japan on Dec. 14, 2016, the entire contents of which are incorporated herein by this reference.

BACKGROUND OF THE INVENTION

1. Field of the Invention

The present invention relates to an endoscope including an endoscope operation portion to and from which a treatment instrument operation portion is attachable and detachable, and an endoscope system.

2. Description of the Related Art

Endoscopes are used in medical fields or industrial fields, and the like. Some of the endoscopes include a bendable bending portion at an insertion portion, for the purpose of improving the insertion property of the insertion portion or improving the observation performance.

The bending portion is configured to bend in a plurality of directions, i.e., up and down directions, or up, down, left and right directions by operating a bending operation member provided at the operation portion.

An endoscope for medical use is capable of performing various kinds of examinations by inserting an elongated insertion portion into a body cavity without a need for incision. In addition, an endoscope including a treatment instrument channel in the insertion portion is capable of performing therapeutic procedure by introducing a treatment instrument into a body cavity through the channel.

When a therapeutic procedure is performed, at least one assistant such as a medical practitioner is present in addition to an operating surgeon. During the therapeutic procedure, two surgeons perform an operation of an endoscope and an operation of a treatment instrument in cooperation with each other.

Specifically, one of the two surgeons performs the operation of the endoscope including medical procedures such as inserting the insertion portion of the endoscope into the kidney, advancing, retreating, or twisting the insertion portion inserted in the kidney under the observation field of view of the endoscope, bending the bending portion, extracting the insertion portion from the kidney together with a basket forceps after catching a calculus.

The other of the two surgeons performs operation of the basket forceps including medical procedures such as inserting the basket forceps into the insertion channel, and catching the calculus by opening and closing the distal end opening/closing portion of the basket forceps.

Furthermore, there is a case where one surgeon performs both of the operation of the endoscope and the operation of the treatment instrument. Specifically, after inserting the basket forceps into the insertion channel, the surgeon mounts the operation portion of the basket forceps to the endoscope operation portion through the adapter.

After that, if the dominant hand of the surgeon is the right hand, for example, the surgeon grasps the endoscope operation portion with the left hand to perform an operation of the bending operation lever and a twisting operation of the insertion portion, and performs an advancing and retreating operation and the extraction operation of the insertion portion and an opening/closing operation of the basket forceps with the right hand.

This is because it is recommended to perform the opening/closing operation of the basket forceps with the dominant hand, since the opening/closing operation of the basket forceps requires a minute operation. Thus, there is a case where only one surgeon performs the medical procedure including both of the operation of the endoscope and the operation of the treatment instrument.

Note that the above-described example is not limited to the case where the basket forceps is used, but is applied to the case where other treatment instruments are used.

Japanese Patent Application Laid-Open Publication No. 2005-168882 discloses a configuration of an endoscopic treatment instrument system in which a holding portion to and from which a treatment instrument is attachable and detachable is provided in the vicinity of an opening of an insertion channel of an endoscope operation portion so as to enable one surgeon to perform an operation of an endoscope and an operation of a treatment instrument.

SUMMARY OF THE INVENTION

An endoscope according to one aspect of the present invention includes: an endoscope operation member provided on a proximal end side of an endoscope insertion portion including a bending portion configured to be inserted into a subject and bendable, the endoscope operation member including a bending operation member configured to cause the bending portion to bend, and a treatment instrument insertion port through which a treatment instrument insertion portion of a treatment instrument is inserted; a first grasping portion provided so as to be positioned on a distal end side with respect to the bending operation member of the endoscope operation member, the first grasping portion being configured to enable the endoscope operation member to be grasped in a first grasping state; a second grasping portion provided so as to extend on a proximal end side of the bending operation member of the endoscope operation member, the second grasping portion being configured to enable the endoscope operation member to be grasped in a second grasping state; and treatment instrument operation portion mounting portions to which an attaching portion provided to a treatment instrument operation portion of the treatment instrument is attachable so as to enable an operation of the bending operation member and an operation of a treatment portion operation member provided to the treatment instrument operation portion of the treatment instrument to be performed with fingers of a hand grasping the endoscope operation member, with the endoscope operation member being grasped in the first grasping state or in the second grasping state, the treatment instrument operation portion mounting portions being formed respectively on the first grasping portion and the second grasping portion.

An endoscope system according to one aspect of the present invention includes an endoscope and a treatment instrument configured to be inserted into the endoscope, the endoscope including: an endoscope operation member provided on a proximal end side of an endoscope insertion portion including a bending portion configured to be inserted into a subject and bendable, the endoscope operation member including a bending operation member configured to cause the bending portion to bend, and a treatment instrument insertion port through which a treatment instrument insertion portion of the treatment instrument is inserted; a first grasping portion provided so as to be positioned on a distal end side with respect to the bending operation member of the endoscope operation member, the first grasping portion being configured to enable the endoscope operation member to be grasped in a first grasping state; a second grasping portion provided so as to extend on a proximal end side of the bending operation member of the endoscope operation member, the second grasping portion being configured to enable the endoscope operation member to be grasped in a second grasping state; and treatment instrument operation portion mounting portions to which an attaching portion provided to a treatment instrument operation portion of the treatment instrument is attachable so as to enable an operation of the bending operation member and an operation of a treatment portion operation member provided to the treatment instrument operation portion of the treatment instrument to be performed with fingers of a hand grasping the endoscope operation member, with the endoscope operation member being grasped in the first grasping state or in the second grasping state, the treatment instrument operation portion mounting portions being formed respectively on the first grasping portion and the second grasping portion, the treatment instrument including the treatment instrument insertion portion to be inserted into the treatment instrument insertion port and the treatment instrument operation portion provided with the attaching portion configured to be attachable to the treatment instrument operation portion attaching portions.

DETAILED DESCRIPTION OF THE PREFERRED EMBODIMENT(S)

Figure 1:
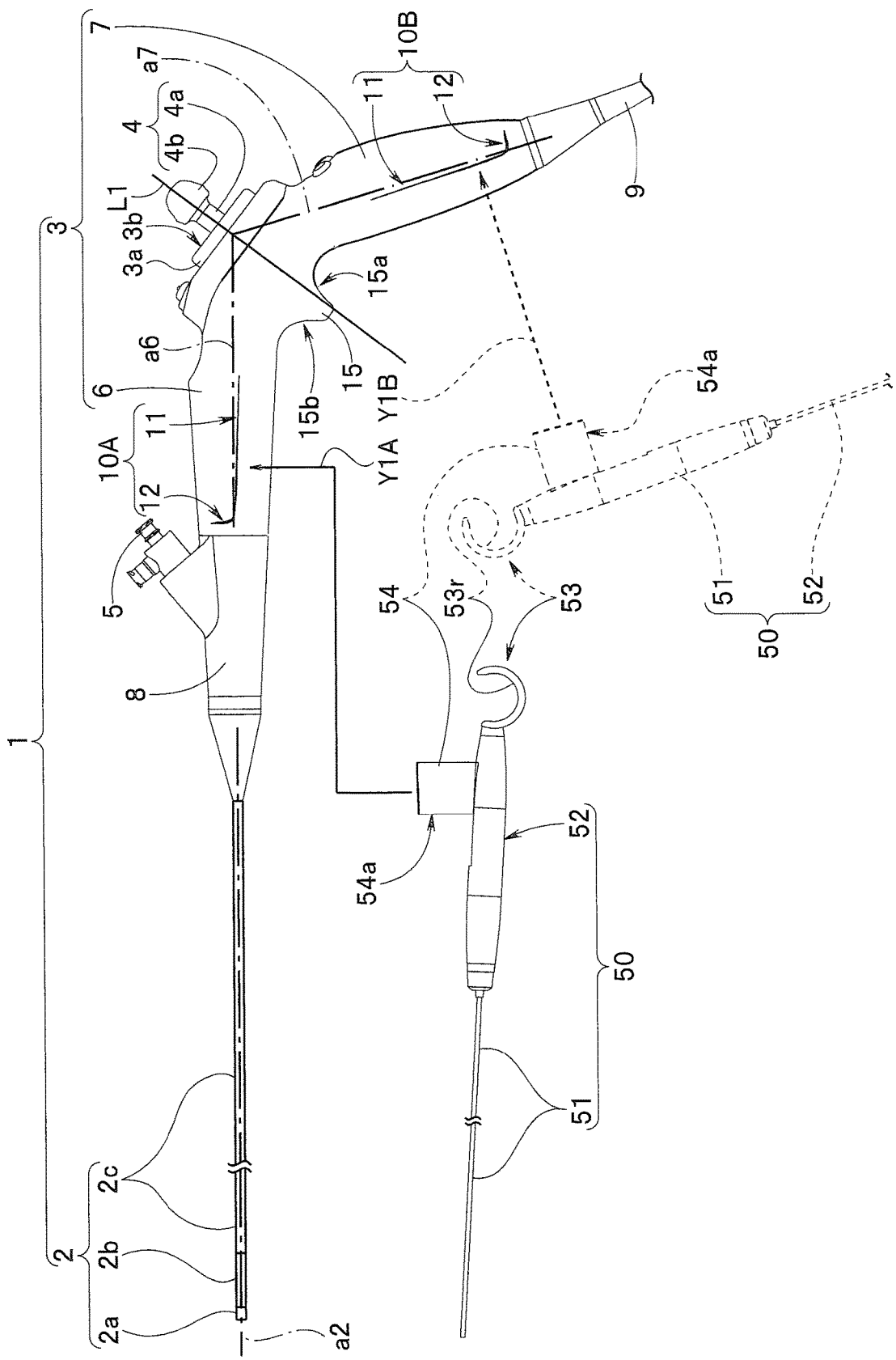
FIG. 1 illustrates configurations of an endoscope and a treatment instrument and a relation between the endoscope and the treatment instrument.

Hereinafter, an embodiment of the present invention will be described with reference to drawings.

Note that, in some of the respective drawings used in the description below, a different scale size is used for each of the constituent elements in order to allow each of the constituent elements to be illustrated in a recognizable size on the drawings. That is, the present invention is not limited to the number, shapes, ratio of the sizes of the constituent elements, and a relative positional relationship among the constituent elements shown in the drawings.

An endoscope 1 shown in FIG. 1 is an endoscope for use in urology, for example.

The endoscope 1 includes an endoscope insertion portion 2 and an endoscope operation portion 3.

The endoscope insertion portion 2 is elongate so as to allow insertion into a subject. The endoscope insertion portion 2 includes in the following order from the distal end side: a distal end portion 2a, a bending portion 2b, and a flexible tube portion 2c.

The distal end portion 2a incorporates an image pickup unit including an image pickup device (not shown) such as CCD, CMOS, and the like. The bending portion 2b is configured to bend in four directions, i.e., up, down, left, and right directions, for example. The flexible tube portion 2c has flexibility and is configured to be bent passively.

The endoscope operation portion 3, which is an endoscope operation member, is provided continuously with the proximal end side of the endoscope insertion portion 2. The endoscope operation portion 3 is a flexed shape and includes a bending operation lever 4 and a treatment instrument insertion port 5 at predetermined positions.

The endoscope operation portion 3 includes a first grasping portion 6 and a second grasping portion 7. The first grasping portion 6 is located on the distal end side with respect to the bending operation lever 4 and constitutes a distal end side of the endoscope operation portion 3, the distal end side being the endoscope insertion portion 2 side. That is, the first grasping portion 6 is located on the proximal end side of the endoscope insertion portion 2 and provided continuously with the proximal end side of the endoscope insertion portion 2 through a port rotating portion 8.

The second grasping portion 7 extends so as to be located on the proximal end side of the bending operation lever 4, which is opposite side of the endoscope insertion portion 2 side on which the first grasping portion 6 is located, and the second grasping portion 7 constitutes the proximal end side of the endoscope operation portion 3. A universal cord 9 is extended from the proximal end side of the second grasping portion 7.

That is, the endoscope operation portion 3 includes the first grasping portion 6 and the second grasping portion 7 that are provided with the bending operation lever 4 located therebetween.

The port rotating portion 8 is provided between the endoscope insertion portion 2 and the first grasping portion 6. Specifically, the distal end side of the port rotating portion 8 is provided continuously with the endoscope insertion portion 2 through a break stopper. On the other hand, the proximal end side of the port rotating portion 8 is rotatably connected to the distal end side of the first grasping portion 6 through a rotation mechanism (not shown). The opening part such as the treatment instrument insertion port 5 is provided on the outer circumferential surface of the port rotating portion 8 so as to protrude from the outer circumferential surface.

The endo scope operation portion 3 is formed in a flexed shape in which a first longitudinal axis a6 which is the longitudinal direction axis of the first grasping portion 6 and a second longitudinal axis a7 which is the longitudinal direction axis of the second grasping portion 7 intersect with each other at a predetermined inferior angle.

The first longitudinal axis a6 of the first grasping portion 6 is parallel to an insertion portion longitudinal axis a2.

The bending operation lever 4 is a bending operation member and configured to be tiltable. The bending operation lever 4 is provided on a superior angle side with respect to the inferior angle. The bending operation lever 4 includes a shaft portion 4a and a finger contact portion 4b. The finger contact portion 4b is provided at a protruding end of the shaft portion 4a. The shaft portion 4a protrudes vertically with respect to a plane 3b of a pedestal 3a provided at a predetermined position of the endoscope operation portion 3.

In the present embodiment, the bending portion 2b is in a linear state when the shaft portion 4a of the bending operation lever 4 is in a neutral state in which the shaft portion 4a stands vertically with respect to the plane 3b. The shaft portion 4a is provided such that the central axis of the shaft portion 4a is positioned on a dividing straight line L1 that halves the superior angle, when the shaft portion 4a is in the neutral state.

With the tilting operation of the shaft portion 4a of the bending operation lever 4 with respect to the dividing straight line L1, the bending portion 2b bends in accordance with the tilting direction and the tilting angle of the shaft portion 4a.

Note that the bending operation lever 4 is configured to be operable with the fingers of either the right hand or the left hand that grasps the endoscope operation portion 3 in a predetermined state.

The treatment instrument insertion port 5 is an opening through which a treatment instrument insertion portion 51 of a basket forceps, for example, as a treatment instrument 50 is inserted. The treatment instrument insertion portion 51 of the treatment instrument 50 is inserted into the treatment instrument insertion port 5, thereafter passed through the inside of the treatment instrument channel (not shown) provided in the endoscope insertion portion 2 or the like, to be led out to the outside from the channel opening (not shown) of the distal end portion 2a.

Note that, in the present embodiment, the treatment instrument 50 includes the treatment instrument operation portion denoted by the reference sign 52, a slider denoted by the reference sign 53, and an attaching portion denoted by the reference sign 54. The slider 53 is a treatment portion operation member and provided slidably in the longitudinal axis direction of the treatment instrument operation portion 52. The slider 53 is slid, to thereby change the state of the basket as the treatment portion into an open state or a closed state.

The slider 53 is provided with an operation ring 53r, for example, which serves as the operation portion. The finger of the hand grasping the grasping portion 6 or 7 is placed on the operation ring 53r, when the operator causes the slider 53 to slide. The attaching portion 54 is provided at a predetermined position of the treatment instrument operation portion 52.

In the present embodiment, the attaching portion 54 is attachable to and detachable from the treatment instrument operation portion 52, but may be provided integrally with the treatment instrument operation portion 52. Note that the reference sign 54a denotes each of insertion portion side end surfaces. The treatment instrument 50 is not limited to the basket forceps, but may be another treatment instrument as long as the slider 53 is provided.

The first grasping portion 6 and the second grasping portion 7 each include an attaching portion mounting portion 10 as the treatment instrument operation portion mounting portion. Hereinafter, in order to clarify the description, the attaching portion mounting portion 10 formed on the first grasping portion 6 is recited as a first mounting portion 10A. On the other hand, the attaching portion mounting portion 10 formed on the second grasping portion 7 is recited as a second mounting portion 10B.

In the present embodiment, the first mounting portion 10A and the second mounting portion 10B are provided at positions symmetrical with respect to the dividing straight line L1.

The attaching portion 54 of the treatment instrument 50 is attachable to the first mounting portion 10A as shown by the solid arrow Y1A, and attachable to the second mounting portion 10B as shown by the dashed arrow Y1B. That is, the configuration of the first mounting portion 10A to which the attaching portion 54 is attached is the same as the configuration of the second mounting portion 10B to which the attaching portion 54 is attached. Therefore, description will be made on the configuration of the first mounting portion 10A, and description on the second mounting portion 10B will be omitted.

Figure 2:
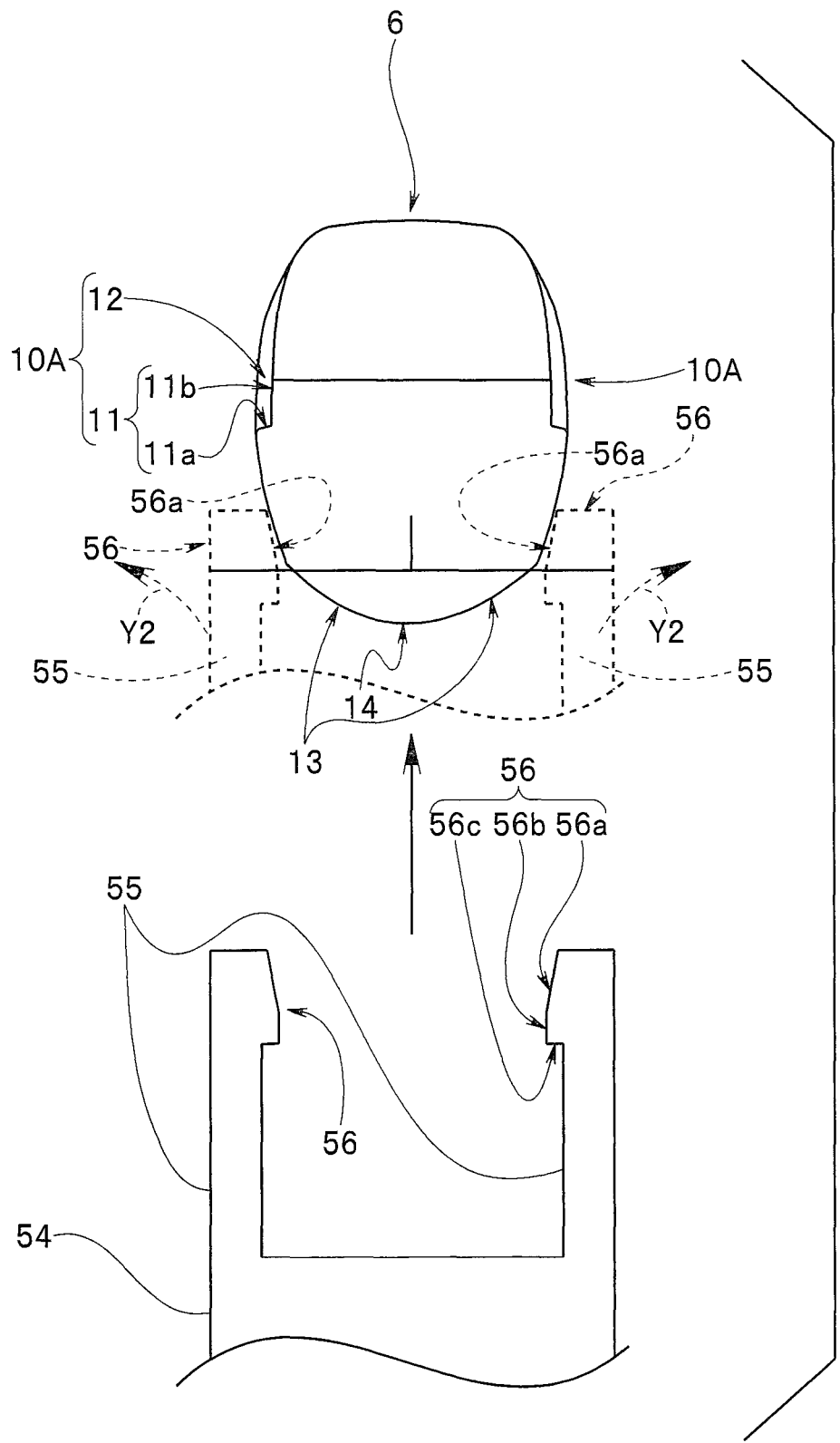
FIG. 2 illustrates an attaching portion mounting portion formed on a grasping portion of the endoscope and an attaching portion provided to the treatment instrument.

Referring to FIGS. 1 and 2, description will be made on the configuration of the first mounting portion 10A and the configuration of the attaching portion 54.

The attaching portion 54 will be described with reference to FIG. 2.

As shown in FIG. 2, a pair of engaging claws 55 are extended from the attaching portion 54. The pair of engaging claws 55 have a predetermined elastic force. Each of the pair of engaging claws 55 includes an engaging protrusion 56 on an extending end side. The reference signs 56a, 56b, 56c denote an inclined surface, an engaging surface, and arranging surface, respectively.

The inclined surfaces 56a of the engaging protrusions 56 are provided so as to face each other. The space between the inclined surfaces 56a facing each other is set to become gradually wider from the root side toward the extending end side of the engaging protrusions 56.

Description will be made on the first mounting portion 10A with reference to FIGS. 1 and 2.

As shown in FIG. 1, the first mounting portion 10A is a pair of step portions, and each of the step portions includes a step surface 11 and positioning surface 12. The pair of step portions are formed on one side surface and on the other side surface which is a surface opposite to the one side surface.

The step surface 11 is provided on the both side surfaces of the first grasping portion 6. The step surface 11 includes a placing surface 11a and a pressing surface 11b. The arranging surface 56c of each of the engaging protrusions 56 is arranged on the placing surface 11a, and the engaging surface 56b is pressed against and arranged on the pressing surface 11b.

The positioning surface 12 is an abutting surface against which the insertion portion side end surface 54a of each of the pair of engaging protrusions 56 abuts.

The reference sign 13 denotes an engaging claw guiding surface provided so as to be located at predetermined positions of the first grasping portion 6 and the second grasping portion 7. The engaging claw guiding surface 13 is a curved surface or a tapered surface, and formed such that the width dimension becomes gradually larger as going from the mounting side surface 14, which is a lower end surface in the drawings, to the placing surface 11a. The inclined surfaces 56a of the engaging protrusions 56 are arranged on the engaging claw guiding surface 13.

The reference sign 15 in FIG. 1 denotes a protrusion portion. The protrusion portion 15 is provided on the inferior angle side of the endoscope operation portion 3 so as to protrude by a predetermined amount. The protrusion portion 15 includes curved surfaces 15a, 15b, each of which serves both as a finger placing portion and a restricting portion. The finger placing portion is configured such that the operator can place his or her fingers of the hand grasping the grasping portion, in contact with the finger placing portion, when grasping the first grasping portion 6 or the second grasping portion 7. The restricting portion is configured to restrict the movement of the slider 53.

Hereinafter, description will be made on attaching of the treatment instrument 50 to the first mounting portion 10A of the first grasping portion 6.

The operator attaches the attaching portion 54 to the first mounting portion 10A, as shown by the arrow Y1A in FIG. 1. At that time, the operator determines the direction of the treatment instrument 50 such that the operation ring 53r is arranged in the vicinity of the protrusion portion 15.

After that, the operator causes the engaging protrusions 56 that constitute the engaging claws 55 of the attaching portion 54 provided on the treatment instrument operation portion 52 to face the engaging claw guiding surface 13 of the first grasping portion 6, as shown in FIG. 2. Then, the operator causes the inclined surfaces 56a of the engaging protrusions 56 to be arranged on the engaging claw guiding surface 13, to push the engaging claws 55 toward the step surfaces 11. As a result, the engaging claws 55 are pushed and advanced along the engaging claw guiding surface 13. At this time, the engaging claws 55 are gradually expanded in the direction of the arrow Y2 in FIG. 2 against the elastic force of the engaging claws 55.

After that, the engaging claws 55 are pushed to the predetermined position, to thereby cause the placing surfaces 56c of the engaging claws 55 to be placed respectively on the placing surfaces 11a of the step surfaces 11 and cause the engaging surfaces 56b to be pressed against and arranged respectively on the pressing surfaces 11b by the elastic force of the engaging claws 55.

Figure 3:
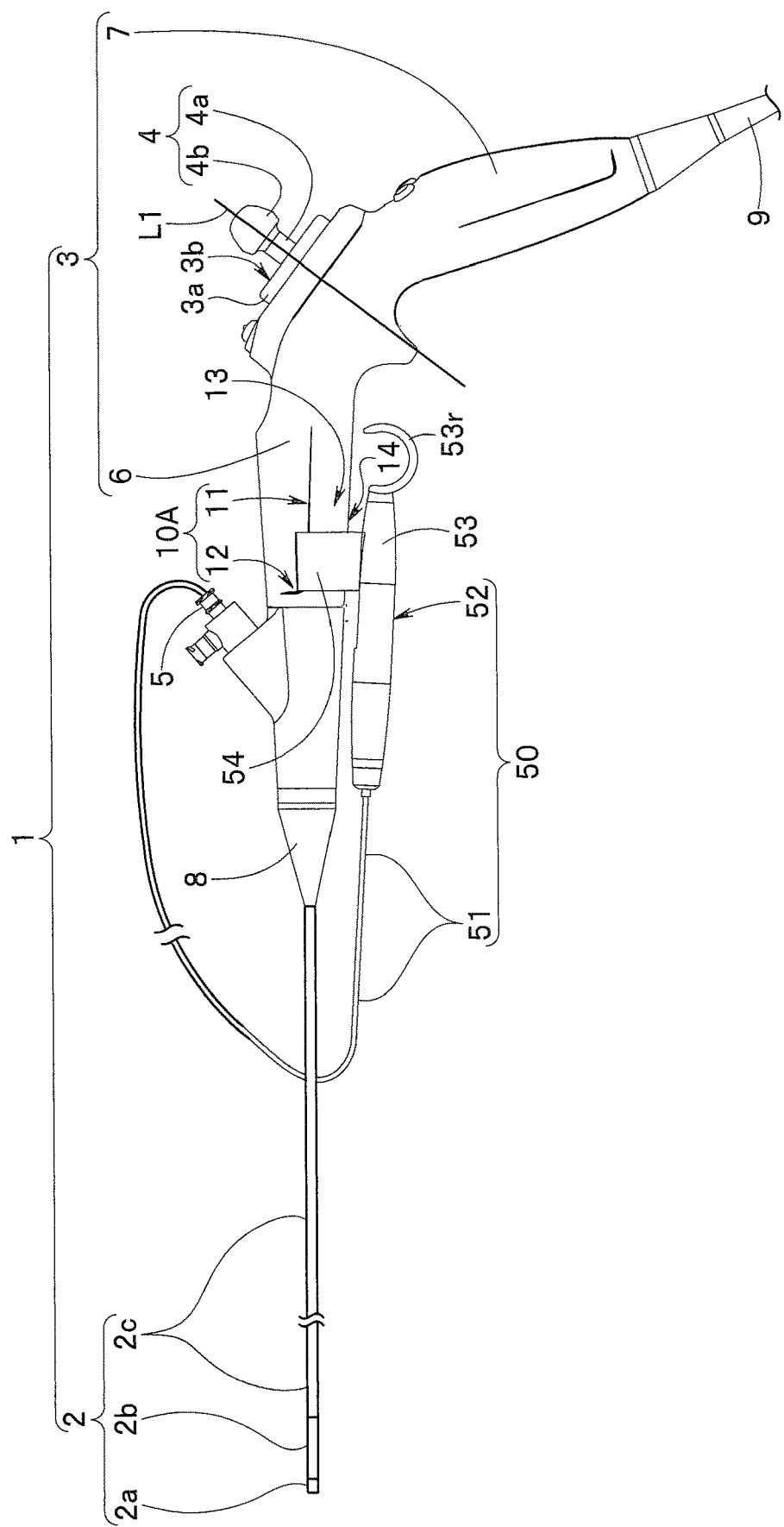
FIG. 3 illustrates a state where a treatment instrument operation portion of the treatment instrument is attached to a first grasping portion of an endoscope operation portion.

Then, the operator brings the insertion portion side end surfaces 54a of the attaching portion 54 into contact with the positioning surfaces 12, respectively. As a result, as shown in FIG. 3, the treatment instrument operation portion 52 of the treatment instrument 50 is attached integrally to the first grasping portion 6 of the endoscope operation portion 3 of the endoscope 1 through the attaching portion 54. At this time, the operation ring 53r is arranged on the second grasping portion 7 side.

Figure 4:
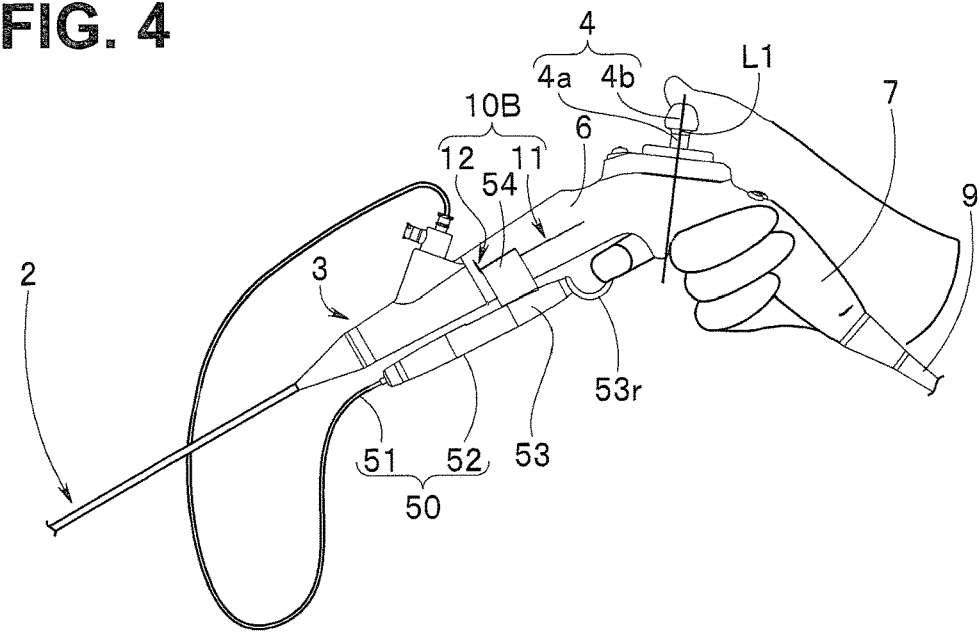
FIG. 4 illustrates a second grasping state in which a second grasping portion is grasped, with the treatment instrument operation portion attached to the first grasping portion.

Thus, in the state where the treatment instrument 50 is attached to the endoscope operation portion 3, the operator places the palm of the right hand and the three fingers, i.e., the little finger, the ring finger, and the middle finger of the right hand on the second grasping portion 7, to thereby be capable of surely and stably grasping the second grasping portion 7 of the endoscope operation portion 3 in the second grasping state, as shown in FIG. 4.

In addition, since the operation ring 53r of the treatment instrument 50 is arranged on the second grasping portion 7 side, when grasping the endoscope operation portion 3 in the second gasping state, the operator places the thumb of the right hand on the finger contact portion 4b of the bending operation lever 4, to thereby be capable of performing tilting operation of the bending operation lever 4 to cause the bending portion 2b to bend, and the operator places the index finger of the right hand in the operation ring 53r, to thereby be capable of performing pulling operation or pushing operation of the slider 53.

Then, the operator places the middle finger of the right hand on the curved surface 15a of the protrusion portion 15 in the second grasping state, which makes it easier for the operator to stably hold the endoscope operation portion 3 with the middle finger, the ring finger, and the little finger, and which makes the range of movement of the index finger and the range of movement of the treatment instrument operation portion 52 coincide with each other, to enable smoother operation of the slider 53.

In this second grasping state, the left hand of the operator is free. Therefore, it is possible for the operator to use his or her left hand only for the advancing/retreating operation of the endoscope insertion portion 2. As a result, the operator does not have to replace the endoscope insertion portion 2 in his or her hand with the treatment instrument operation portion 52 or vice versa.

Next, description will be made on attaching of the treatment instrument 50 to the second mounting portion 10B of the second grasping portion 7.

The operator attaches the attaching portion 54 to the second mounting portion 10B as shown in the arrow Y1B in FIG. 1. At that time, the operator determines the direction of the treatment instrument 50 such that the operation ring 53r is arranged in the vicinity of the protrusion portion 15.

After that, similarly as described above, the operator causes the engaging protrusions 56 that constitute the engaging claws 55 of the attaching portion 54 provided on the treatment instrument operation portion 52 to face the engaging claw guiding surface 13 of the second grasping portion 7. The operator causes the inclined surfaces 56a of the engaging protrusions 56 to be arranged on the engaging claw guiding surface 13 to push the engaging claws 55. Then, the placing surfaces 56c of the engaging claws 55 are placed respectively on the placing surfaces 11a of the step surfaces 11, and the engaging surfaces 56b are pressed against and arranged respectively on the pressing surfaces 11b.

Figure 5:
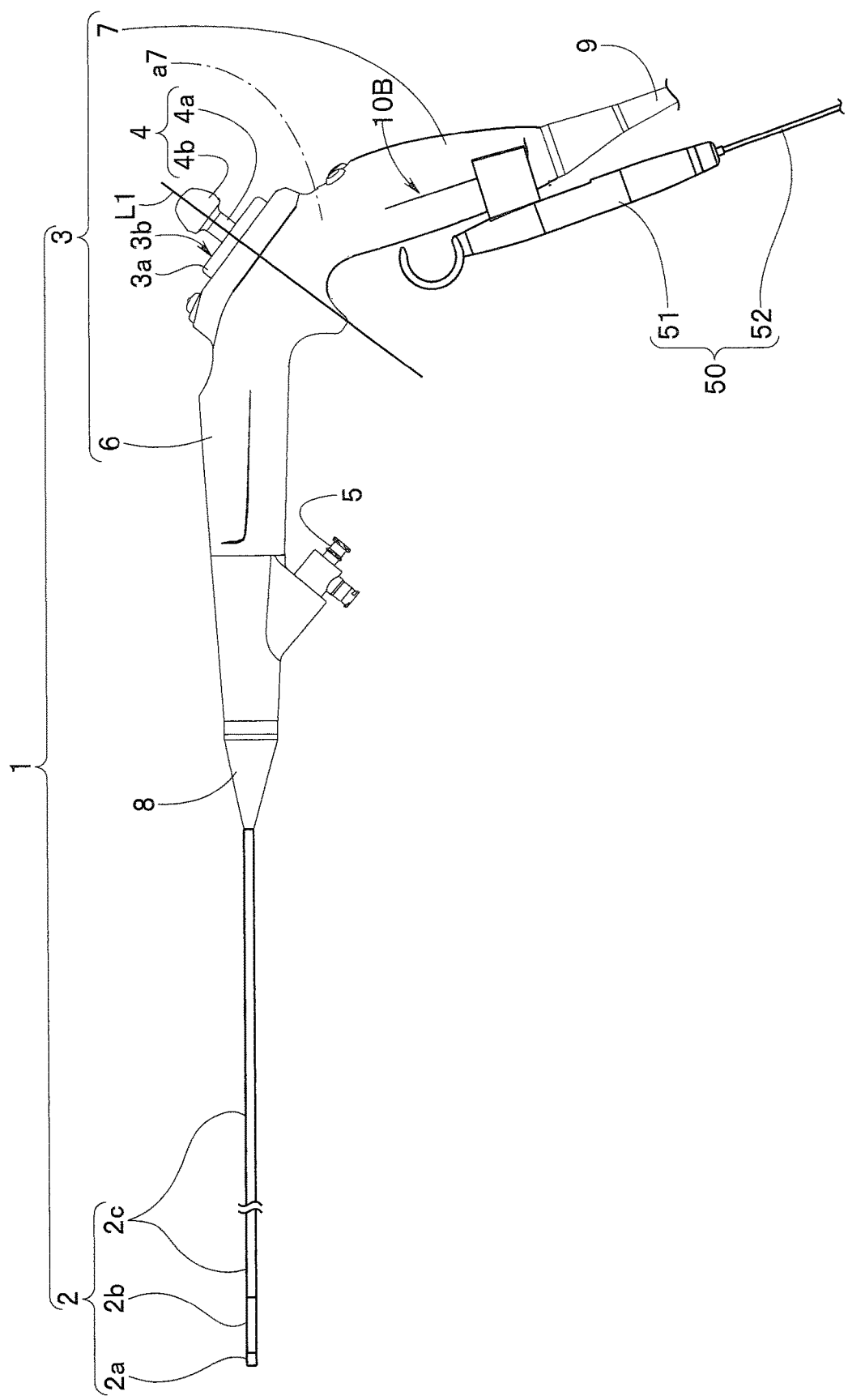
FIG. 5 illustrates a state in which the treatment instrument operation portion of the treatment instrument is attached to the second grasping portion of the endoscope operation portion.

After that, the operator brings the insertion portion side end surfaces 54a of the attaching portion 54 into contact with the positioning surfaces 12, respectively. As a result, as shown in FIG. 5, the treatment instrument operation portion 52 of the treatment instrument 50 is attached integrally to the second grasping portion 7 of the endoscope operation portion 3 of the endoscope 1 through the attaching portion 54. At this time, the operation ring 53r is arranged on the first grasping portion 6 side.

Figure 6:
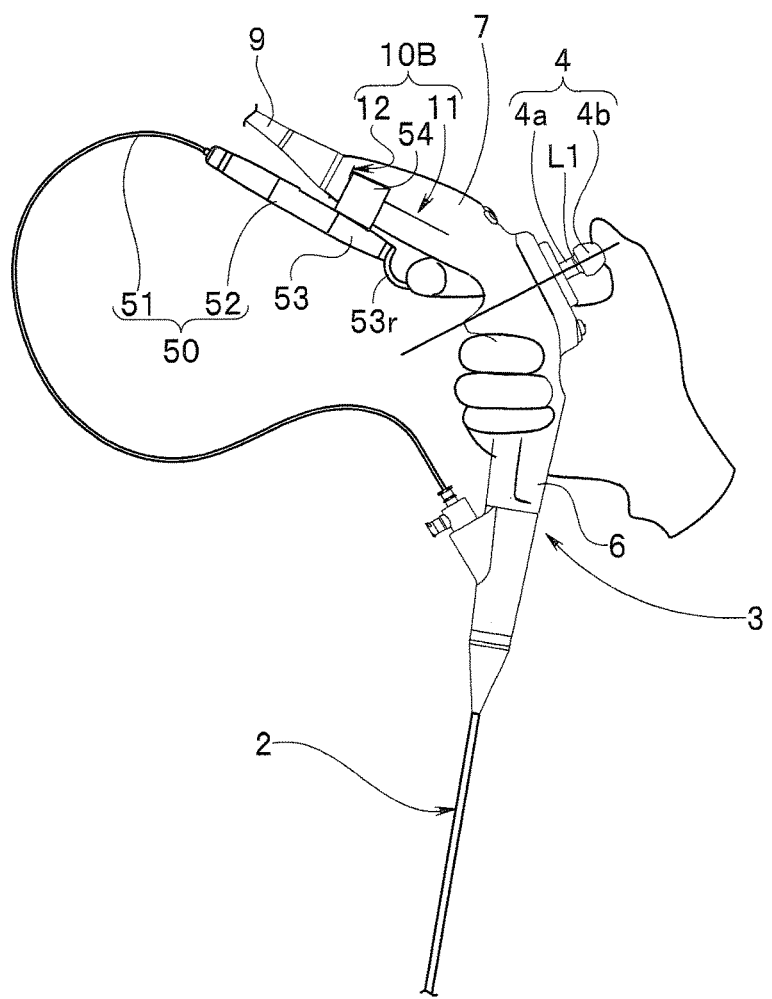
FIG. 6 illustrates a first grasping state in which the first grasping portion is grasped, with the treatment instrument operation portion attached to the second grasping portion.

Thus, in the state where the treatment instrument 50 is attached to the endoscope operation portion 3, the operator places the palm of the right hand and the three fingers, i.e., the little finger, the ring finger, and the middle finger of the right hand on the first grasping portion 6, to thereby be capable of surely and stably grasping the first grasping portion 6 of the endoscope operation portion 3 in the first grasping state, as shown in FIG. 6.

In addition, since the operation ring 53r of the treatment instrument 50 is arranged on the first grasping portion 6 side, when grasping the endoscope operation portion 3 in the first gasping state, the operator places the thumb of the right hand on the finger contact portion 4b of the bending operation lever 4, to thereby be capable of performing tilting operation of the bending operation lever to cause the bending portion 2b to bend, and the operator places the index finger of the right hand in the operation ring 53r, to thereby be capable of performing pulling operation or pushing operation of the slider 53.

As a result, also in the first grasping state, the operator places the middle finger of the right hand on the curved surface 15a of the protrusion portion 15, which makes it easier for the operator to stably hold the endoscope operation portion 3 with the middle finger, the ring finger, and the little finger, and which makes the range of movement of the index finger and the range of movement of the treatment instrument operation portion 52 coincide with each other, to enable smoother operation of the slider 53.

In also this first grasping state, the left hand of the operator is free. Therefore, it is possible for the operator to use his or her left hand only for the advancing/retreating operation of the endoscope insertion portion 2. As a result, the operator does not have to replace the endoscope insertion portion 2 in his or her hand with the treatment instrument operation portion 52 or vice versa.

Note that, in the above-described embodiment, it is supposed that the operator grasps the first grasping portion 6 and the second grasping portion 7 of the endoscope operation portion 3 with the right hand. However, even if the operator grasps the first grasping portion 6 and the second grasping portion 7 with the left hand, the same grasping property and operability can be obtained. In addition, it is supposed that the operator performs pulling operation or pushing operation of the slider 53 with the index finger of the hand grasping the grasping portion. However, the operator may operates the slider 53 with another finger.

In addition, the treatment instrument insertion portion 51 of the treatment instrument 50 is inserted from the treatment instrument insertion port 5 into the treatment instrument channel, after the treatment instrument operation portion 52 is integrally attached to the first grasping portion 6 or the second grasping portion 7 of the endoscope operation portion 3, or the treatment instrument insertion portion 51 is inserted, in advance, from the treatment instrument insertion port 5 into the treatment instrument channel by a predetermined amount before the treatment instrument operation portion 52 is attached to the endoscope operation portion 3.

Thus, the endoscope operation portion 3 is configured by including the first grasping portion 6 on which the first mounting portion 10A is formed and the second grasping portion 7 on which the second mounting portion 10B is formed, with the bending operation lever 4 located between the first grasping portion and the second grasping portion. The endoscope operation portion 3 is formed in the flexed shape in which the first longitudinal axis a6 of the first grasping portion 6 and the second longitudinal axis a7 of the second grasping portion 7 intersect with each other at the predetermined inferior angle. The bending operation lever 4 provided so as to stand on the superior angle side, and the central axis of the shaft portion 4a of the bending operation lever 4 is positioned on the dividing straight line L1 which halves the superior angle. In addition, the first mounting portion 10A and the second mounting portion 10B are provided in the positional relationship symmetrical with respect to the dividing straight line L1. Furthermore, the treatment instrument operation portion 52 includes the attaching portion 54 attachable to the first mounting portion 10A or the second mounting portion 10B.

Therefore, in the state where the attaching portion 54 is attached to the first mounting portion 10A, the operator can grasp the endoscope operation portion 3 in the second grasping state in which the operator grasps the second grasping portion 7. On the other hand, in the state where the attaching portion 54 is attached to the second mounting portion 10B, the operator can grasp the endoscope operation portion 3 in the first grasping state in which the operator grasps the first grasping portion 6.

In the first grasping state and the second grasping state, the operator can perform the tilting operation of the bending operation lever with the thumb of the hand grasping the grasping portion, and can perform pulling operation or pushing operation of the slider 53 with the index finger of the hand grasping the grasping portion.

That is, with the endoscope 1 according to the present embodiment, the operator can grasp the endoscope operation portion 3 with one hand or the other hand selectively in the first grasping state or the second grasping state. In addition, in the first grasping state and the second grasping state, the operator can operate the bending operation lever 4 with the thumb of the hand grasping the grasping portion and operate the slider 53 with the index finger of the hand. Therefore, the operator can use the hand not grasping the endoscope operation portion 3 only for the advancing/retreating operation of the endoscope insertion portion 2.

Note that the present invention is not limited only to the above-mentioned embodiment, but may be modified and embodied in various forms without departing from the scope of the present invention.

According to the present invention, it is possible to provide the endoscope with excellent grasping property and operability, which enables the first grasping state and the second grasping state to be selected, and enables the operation of the bending operation member and the operation of the operation member of the treatment instrument operation portion to be performed with the fingers of the one hand grasping the endoscope operation portion.

What is claimed is:

1. An endoscope comprising:
   an endoscope operation member provided on a proximal end side of an endoscope insertion portion, the endoscope insertion portion including a bending portion configured to be inserted into a subject and bendable, the endoscope operation member including a bending operation lever configured to cause the bending portion to bend, and a treatment instrument insertion port through which a treatment instrument insertion portion of a treatment instrument is inserted;
   a first grasping portion provided so as to be positioned on a distal end side with respect to the bending operation lever, the first grasping portion being configured to enable the endoscope operation member to be grasped in a first grasping state;
   a second grasping portion provided so as to extend on a proximal end side of the bending operation lever, the second grasping portion being configured to enable the endoscope operation member to be grasped in a second grasping state;
   a first mount configured to attach to a treatment instrument operation portion of the treatment instrument, the treatment instrument operation portion having a longitudinal axis, the first mount being provided on the first grasping portion; and
   a second mount configured to attach the treatment instrument operation portion, the second mount being provided on the second grasping portion, wherein
   when the treatment instrument operation portion is attached to the first mount, the treatment instrument operation portion is attached along the first grasping portion such that a treatment instrument operation slider is arranged on a side of the bending operation lever, the treatment instrument operation slider being provided at one end of the treatment instrument operation portion and configured to be slidable with respect to the longitudinal axis of the treatment instrument operation portion, so as to enable an operation of the bending operation lever and an operation of the treatment instrument operation slider to be performed with fingers of a hand grasping the endoscope operation member while grasping the endoscope operation member with the hand in the second grasping state, and
   when the treatment instrument operation portion is attached to the second mount, the treatment instrument operation portion is attached along the second grasping portion such that the treatment instrument operation slider is arranged on a side of the bending operation lever, so as to enable the operation of the bending operation lever and the operation of the treatment instrument operation slider to be performed with the fingers of the hand grasping the endoscope operation member while grasping the endoscope operation member with the hand in the first grasping state.

2. The endoscope according to claim 1, wherein the endoscope operation member is formed in a flexed shape having an apex at a crossing point between a longitudinal axis of the first grasping portion and a longitudinal axis of the second grasping portion, in which the longitudinal axis of the first grasping portion and the longitudinal axis of the second grasping portion intersect with each other to define an inferior angle and a superior angle between the longitudinal axis of the first grasping portion and the longitudinal axis of the second grasping portion, the bending operation lever is disposed on a side of the intersection between the longitudinal axis of the first grasping portion and the longitudinal axis of the second grasping portion which forms the superior angle, and the first mount and the second mount are provided at positions symmetrical with respect to a straight line that halves the inferior angle.

3. The endoscope according to claim 2, wherein the straight line that halves the inferior angle and a central axis of a shaft portion of the bending operation lever coincide with each other when the bending operation lever is in a neutral state.

4. The endoscope according to claim 2, wherein the treatment instrument operation portion is attached on a side of the intersection between the longitudinal axis of the first grasping portion and the longitudinal axis of the second grasping portion which forms the inferior angle.

5. The endoscope according to claim 1, wherein the treatment instrument operation portion includes an engaging claw with which the treatment instrument operation portion is mountable to each of the first mount and the second mount, the first mount includes a first step portion configured to be engaged with the engaging claw, and the second mount includes a second step portion configured to be engaged with the engaging claw.

6. The endoscope according to claim 1, wherein:

the first mount comprises a first indented surface formed on each of opposing sides of the first grasping section, each of the first indented surfaces terminating in a first step formed between each first indented surface and a first exterior surface of the first grasping section, the opposing first indented surfaces being formed at a predetermined first distance apart from each other; and the second mount comprises a second indented surface formed on each of opposing sides of the second grasping section, each of the second indented surfaces terminating in a second step formed between each second indented surface and a second exterior surface of the second grasping section, the opposing second indented surfaces being formed at a predetermined second distance apart from each other.

7. The endoscope according to claim 6, wherein the first distance is equal to the second distance.

8. An endoscope system comprising, an endoscope; and a treatment instrument configured to be inserted into the endoscope, the endoscope comprising:

an endoscope operation member provided on a proximal end side of an endoscope insertion portion, the endoscope insertion portion including a bending portion configured to be inserted into a subject and bendable, the endoscope operation member including a bending operation lever configured to cause the bending portion to bend, and a treatment instrument insertion port through which a treatment instrument insertion portion of the treatment instrument is inserted;

a first grasping portion provided so as to be positioned on a distal end side with respect to the bending operation lever, the first grasping portion being configured to enable the endoscope operation member to be grasped in a first grasping state;

a second grasping portion provided so as to extend on a proximal end side of the bending operation lever, the second grasping portion being configured to enable the endoscope operation member to be grasped in a second grasping state;

a first mount configured to attach to a treatment instrument operation portion of the treatment instrument, the first mount being provided on the first grasping portion; and a second mount configured to attach to the treatment instrument operation portion, the second mount being provided on the second grasping portion, the treatment instrument comprising:

the treatment instrument insertion portion to be inserted into the treatment instrument insertion port;

the treatment instrument operation portion having a longitudinal axis and configured to attach to the first mount and to attach to the second mount;

a treatment instrument operation slider provided at one end of the treatment instrument operation portion, the treatment instrument operation slider being configured to be slidable with respect to the longitudinal axis of the treatment instrument operation portion, wherein when the treatment instrument operation portion is attached to the first mount, the treatment instrument operation portion is attached along the first grasping portion such that the treatment instrument operation slider is arranged on a side of the bending operation lever, so as to enable an operation of the bending operation lever and an operation of the treatment instrument operation slider to be performed with fingers of a hand grasping the endoscope operation member while grasping the endoscope operation member with the hand in the second grasping state, and when the treatment instrument operation portion is attached to the second mount, the treatment instrument operation portion is attached along the second grasping portion such that the treatment instrument operation slider is arranged on a side of the bending operation lever, so as to enable the operation of the bending operation lever and the operation of the treatment instrument operation slider to be performed with the fingers of the hand grasping the endoscope operation member while grasping the endoscope operation member with the hand in the first grasping state.

\* \* \* \* \*